United States Patent
Berg et al.

(10) Patent No.: US 6,838,061 B1
(45) Date of Patent: Jan. 4, 2005

(54) REACTOR FOR CARRYING OUT GAS-LIQUID, LIQUID, LIQUID-LIQUID OR GAS-LIQUID-SOLID CHEMICAL REACTIONS

(75) Inventors: Stefan Berg, Frankenthal (DE); Peter Zehner, Ludwigshafen (DE); Regina Benfer, Altrip (DE); Jörn Müller, Ludwigshafen (DE); Michael Nilles, Ludwigshafen (DE); Ralf Schulz, Speyer (DE); Dieter Stützer, Dudenhofen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/831,402
(22) PCT Filed: Nov. 23, 1999
(86) PCT No.: PCT/EP99/09059
§ 371 (c)(1),
(2), (4) Date: May 9, 2001
(87) PCT Pub. No.: WO00/30743
PCT Pub. Date: Jun. 2, 2000

(30) Foreign Application Priority Data

Nov. 26, 1998 (DE) .......................................... 198 54 637

(51) Int. Cl.$^7$ ................................................. F28D 7/00
(52) U.S. Cl. ....................................... 422/198; 422/200
(58) Field of Search ................................ 422/198, 200, 422/201, 187

(56) References Cited

U.S. PATENT DOCUMENTS 3,723,545 A * 3/1973 Nagel et al. ................. 568/855

(List continued on next page.)

FOREIGN PATENT DOCUMENTS

| DE | 1 442 821 | 12/1968 |
|---|---|---|
| DE | 32 06 661 | 9/1983 |
| DE | 34 45 904 | 8/1986 |
| DE | 43 23 687 | 1/1995 |
| EP | 0 263 935 | 4/1988 |
| GB | 1013888 | 12/1965 |
| GB | 1133483 | 3/1966 |
| GB | 2 222 098 | 2/1990 |
| JP | 63043920 | 2/1988 |

OTHER PUBLICATIONS

Altensen et al. "Strahlgetriebener Schlaufenreaktor" BIOforum vol. 1, (1993) pp. 18–22.
Cramers et al. "Hydrodynamics and Mass Transfer Characterisitcs of Loop–Venture Reactor with a Downflow Liquid Jet Ejector" Chemical Engineering Science vol. 47, No. 13/14 (1992) pp. 3557–3564.

*Primary Examiner*—M. Alexandra Elve
(74) *Attorney, Agent, or Firm*—Keil & Weinkauf

(57) ABSTRACT

A reactor (1) of high cylindrical construction for continuously carrying out gas-liquid, liquid-liquid or gas-liquid-solid reactions, provided with a downward-directed jet nozzle (2) via which the starting materials and the reaction mixture are fed in and which is located in the upper region of the reactor, and provided with an offtake (3), preferably in the lower region of the reactor, via which the reaction mixture is conveyed via an external circuit back to the jet nozzle (2) by means of a pump (P), wherein a guide tube (4) which extends essentially over the total length of the reactor (1) with the exception of the reactor ends and has a cross-sectional area in the range from one tenth to one half of the cross-sectional area of the reactor (1) is located concentrically in the reactor (1), and the jet nozzle (2) is located above the upper end of the guide tube (4), preferably at a distance of from one eighth of the guide tube diameter to one guide tube diameter, or projects into the guide tube (4) to a depth up to a plurality of guide tube diameters is proposed. A heat exchanger, in particular a heat exchanger having heat exchange tubes (6), preferably running parallel to the guide tube, welded in between plates (5), is integrated into the annular space.

9 Claims, 1 Drawing Sheet

U.S. PATENT DOCUMENTS 4,234,560 A * 11/1980 Kuerten et al. ............. 423/659
5,154,898 A * 10/1992 Ajinkya et al. ............. 422/227
5,387,396 A    2/1995 Dallmeyer et al. ......... 422/106
5,563,296 A   10/1996 Zarnack et al. ............. 564/222

* cited by examiner

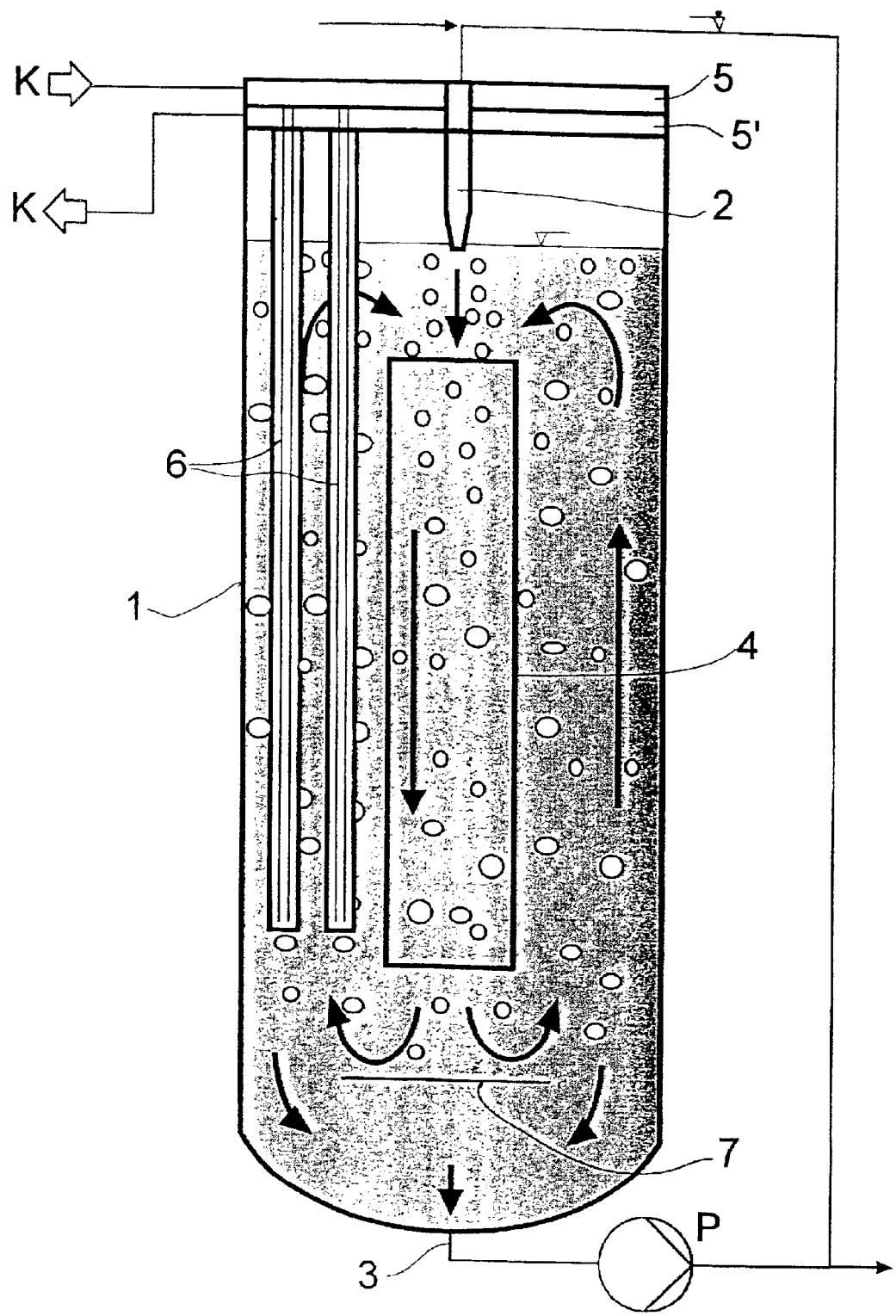

REACTOR FOR CARRYING OUT GAS-LIQUID, LIQUID, LIQUID-LIQUID OR GAS-LIQUID-SOLID CHEMICAL REACTIONS

The present invention relates to a reactor for continuously carrying out gas-liquid, liquid-liquid or gas-liquid-solid reactions, to a process and to a use of the reactor.

Gas-liquid mass transfer and the removal of heat are the rate-determining steps in many chemical processes. To improve mass transfer at the phase interface, the use of ejectors, i.e. devices which utilize the kinetic energy of a high-velocity liquid jet to draw in and disperse the gas phase, has been proposed for such reactions. The high energy input creates high turbulence and generates high shear forces in the ejector, so that the gas is dispersed in the form of very small bubbles, i.e. a very high gas-liquid interfacial area per unit volume is generated. In the literature, values of from 40 000 to 70 000 $m^2/m^3$ for the phase boundary area per unit volume are described for ejectors, compared to from 500 to 2 500 in the overall system, i.e. outside the ejector (cf Chem. Eng. Sci. Vol. 47, No. 13/14 pp. 3557 if, 1992).

Apparatuses for carrying out gas-liquid or gas-liquid-solid reactions using ejectors are known as loop venturi reactors and are described, for example, in DE-A4323687 in conjunction with a continuous process for preparing aromatic diamines and polyamines by catalytic hydrogenation of the corresponding polynitro compounds. The ejector, i.e. a two-fluid jet nozzle with fixed impulse exchange tube and diffuser in which circulated liquid mixture and gaseous reactant (hydrogen) are brought into contact, is located at the end of the loop venturi reactor. A proportion of the length of the ejector projects through the gas-liquid phase interface into the liquid. The gas dispersion power is high in the ejector itself, but not in the remaining reactor volume which, in terms of flow and residence time behavior, has pure bubble column characteristics. In this reactor volume outside the ejector, small and large random eddies with comparatively low mass transfer keep the catalyst in the suspended state. The gas content in the reactor is established predominantly on the basis of the properties of the materials but to a lesser extent also on the basis of the initial dispersion. The heat of reaction which is liberated is removed via an external heat exchanger in the pump circuit.

EP-A-263 935 describes stirred tank reactors for carrying out strongly exothermic reactions, in which the heat liberated is removed via Field tube heat exchangers at the place where it arises. As is known, the term Field tube heat exchanger refers to heat exchangers which have a bundle of parallel double-walled tubes, where the ends of the outer tubes projecting into the reactor space are closed and the corresponding ends of the inner tubes are open, so that the heat exchange medium flows via a feed space located outside the reactor space into the inner tubes and flows out via the space between inner and outer tubes and an outlet space. Such heat exchangers have a high ratio of heat exchange area to volume of the reaction space and are thus particularly effective for removing the heat of reaction liberated. However, the process described has the disadvantage that mixing of the phases is not ensured, with the consequence that there is increased occurrence of uncontrollable secondary reactions resulting in a reduction in yield and that the cooling surfaces become covered with resinous compounds and/or catalyst.

It is an object of the present invention to provide a reactor for gas-liquid, liquid-liquid or gas-liquid-solid reactions which ensures intensive mixing of the phases in the entire reaction volume and thus ensures improved efficiency and an improved space-time yield.

In one embodiment, it is also an object of the invention to ensure that the reactor is largely isothermal, i.e. there is a very small temperature gradient over the height of the reactor.

A further object of the invention is to provide a continuous process for gas-liquid, liquid-liquid or gas-solid reactions using a reactor according to the present invention.

The present invention starts out from a reactor for gas-liquid or gas-liquid-solid reactions having a high cylindrical construction provided with a downward-directed jet nozzle via which the starting materials and the reaction mixture are fed in and which is located in the upper region of the reactor, and provided with an offtake, preferably in the lower region of the reactor, via which the reaction mixture is conveyed via an external circuit back to the jet nozzle by means of a pump.

In the reactor of the present invention, a guide tube which extends essentially over the total length of the reactor with the exception of the reactor ends and has a cross-sectional area in the range from one tenth to one half of the cross-sectional area of the reactor is located concentrically in the reactor, and the jet nozzle is located above the upper end of the guide tube, preferably at a distance of from one eighth of the guide tube diameter to one guide tube diameter, or projects into the guide tube to a depth up to a plurality of guide tube diameters, and a heat exchanger, in particular a heat exchanger having heat exchange tubes, preferably running parallel to the guide tube, welded in between plates, is integrated into the annular space.

It has been found that the mass transfer and heat transport limitations are largely or completely eliminated and the overall reaction thus proceeds under purely kinetic control in such a reactor.

The solution provided by the present invention, according to which the major part of the reaction mixture is conveyed in a directed internal loop and only a small part of the reaction mixture which is necessary for driving the loop flow is pumped around an external circuit, is energetically advantageous.

As a result of the flow conditions being unambiguously defined in the entire reactor volume, i.e. the most important parameters for design of the reactor, viz. flow velocities, gas contents, backmixing, mixing time and residence time behavior, can be determined sufficiently precisely, the reactor of the present invention is capable of direct scale-up.

The term jet nozzle refers, as is known, to a tube which tapers in the flow direction; the jet nozzle can be configured as a three-fluid or two-fluid nozzle, optionally with impulse exchange tube and diffuser, or as a single-fluid nozzle.

When using a single-fluid nozzle, one or more gaseous reactants can additionally be introduced into the gas space at the top of the reactor or via suitable facilities, preferably via one or more, in particular from one to three, annular pipes having a plurality of orifices, particularly in the lower region of the reactor or distributed over the height of the reactor, into the annular space between guide tube and interior wall of the reactor. However, the gas can also be fed in below the impingement plate or directly into the gas space above the single-fluid nozzle. The buoyancy generated by the gas bubbles helps to drive the internal loop flow.

The offtake for the reaction mixture can in principle be located at any height on the reactor, preferably in the lower region of the reactor, particularly preferably at the bottom of the reactor. Part of the reaction mixture is taken off via the offtake by means of a pump and, optionally after solid components, in particular suspended catalyst, have been separated off, for example in a crossflow filter, fed back to the jet nozzle in the upper part of the reactor.

For the purposes of the present invention, the term guide tube refers to an internal tube which is located concentrically in the vertical cylindrical reactor and extends over virtually the entire length of the reactor with the exception of the reactor ends. The upper end of the guide tube always has to be covered with liquid, i.e. it must be located below the upper gas separation space which, according to the present invention, makes up from about 3 to 15% of the total volume of the reactor, in particular from 5 to 7% of the total volume of the reactor. The upper end of the guide tube has to be at a distance from the downward directed jet nozzle whose axis is preferably coincident with that of the guide tube. The relative positioning of nozzle and guide tube and the internal fill level can be used to set the gas content in the reaction mixture.

The jet nozzle preferably has its opening in the region of the interface between continuous gaseous and liquid phases, i.e. the surface of the liquid. In this case, the gas content in the reaction volume can be altered within certain limits by raising or lowering the level of liquid. If, for example, the nozzle is dipped in the liquid by raising the level of liquid, the gas content of the reaction mixture becomes smaller, while lowering the level of liquid below the outlet of the jet nozzle results in larger amounts of gas being drawn into the reaction volume.

The guide tube preferably has a cross-sectional area in the range from one tenth to one half of the cross-sectional area of the reactor. The lower end of the guide tube is in the lower region of the reactor, preferably in the region of the cylindrical end of the reactor.

A heat exchanger, in particular a heat exchanger having heat exchange tubes, preferably running parallel to the guide tube, welded in between plates, is integrated into the annular space between guide tube and interior wall of the reactor. This ensures, particularly in the case of strongly exothermic reactions, that the reactor is largely isothermal, i.e. has a very small temperature gradient over the height of the reactor, since the heat of reaction is removed where it arises. In addition, the reliability of the process is improved compared to a process employing cooling in the external circuit, since the reactor cooling still functions if the pump for the external circuit fails. If the cooling water supply fails, cooling still functions until all the cooling water in the heat exchange tubes has been vaporized.

However, it is also possible to integrate heat exchangers having a different construction, in particular Field tube heat exchangers, into the annular space.

The reactor preferably has an aspect ratio, i.e. the ratio of length (l) to diameter (d), of from 3 to 10, more preferably from 6 to 10. The reactor can be constructed with this high aspect ratio because of the directed internal loop flow. As a result of the high aspect ratio, the gas content in the reaction volume can be altered by means of only small changes in the amount of liquid in the reactor, because this alters the relative positioning of jet nozzle and liquid surface.

The ratio of the diameters of the guide tube and the reactor is preferably in the range from 0.25 to 0.5, preferably in the range from 0.28 to 0.33.

The lower region of the reactor is preferably provided with an impingement plate installed below the lower end of the guide tube, essentially perpendicular to the guide tube and preferably at a distance of from one to two guide tube diameters from the guide tube. The impingement plate is preferably configured as a disk having a diameter greater than the diameter of the guide tube and smaller than the internal diameter of the reactor and a thickness determined by the mechanical strength of the preferably metallic material of construction, i.e. in the range of about 5–10 mm. The impingement plate not only has the function of reversing the flow but also has the task of preventing gas bubbles from being carried into the external circuit and damaging the pump.

The present invention also provides a continuous process for carrying out gas-liquid or gas-liquid-solid reactions in a reactor as described above, wherein the major part of the reaction mixture, corresponding to from 2 to 30 times, preferably from 5 to 10 times, the volume flow of the reaction mixture pumped in the external circuit, flows in an internal loop through the guide tube from the top downward and through the annular space between guide tube and interior reactor wall from the bottom upward. For the purposes of the present invention, the expression internal loop (flow) refers to a circulation of the reaction mixture within the reactor which is driven by the liquid jet produced by the downward-directed jet nozzle located in the upper region of the reactor. This downward-directed liquid jet produces a downward flow in the guide tube which, after leaving the guide tube, is deflected in the lower region of the reactor and is directed upward in the annular space between guide tube and interior wall of the reactor. At the upper end of the guide tube, the liquid is once again drawn in by the driving jet, mixed with this and turned downward again. The loop flow can be assisted by addition of one or more gaseous reactants into the annular space between guide tube and interior wall of the reactor by exploiting the buoyancy of the gas.

The liquid jet disperses the circulating gas present in the form of gas bubbles in the two-phase flow at the upper end of the guide tube, in the vicinity of the jet nozzle, as a result of which very high gas transfer coefficients and phase boundary areas per unit volume are achieved. Furthermore, the liquid jet draws in the gas from the gas separation space in the upper part of the reactor and disperses it.

The apparatus and process of the present invention are particularly useful for highly exothermic gas-liquid, liquid-liquid or gas-liquid-solid reactions, preferably suspension-catalyzed hydrogenations, organic oxidations, ethoxylations, propoxylations or aldol condensations.

The application of the process and apparatus of the present invention to the abovementioned reactions makes it possible to achieve better space-time yields, milder reaction conditions, in particular in respect of the pressure and possibly the temperature, reduced reaction volumes, lower production costs due to energy savings, possibly reduced capital costs and improved safety.

The invention is illustrated below by means of a FIGURE and an example.

The single FIGURE shows a longitudinal section through a reactor 1 according to the present invention having a jet nozzle 2 via which the starting materials and the reaction mixture can be fed in and which is locked in the upper region of the reactor and having an offtake 3 in the lower region of the reactor, via which the reaction mixture is conveyed in an external circuit by means of a pump P and fed back to the jet nozzle 2. A concentric guide tube 4 extending over the major part of the reactor length with the exception of the reactor ends is located in the reactor 1. The FIGURE shows an impingement plate 7, which is preferably present, below the lower end of the guide tube 4. A heat exchanger which is depicted in the FIGURE as a Field tube heat exchanger with feed space 5 and discharge space 5' for the coolant K and with heat exchange tubes 0.6 is also preferably provided. In a further preferred embodiment, the heat exchanger can be in the form of heat exchange tubes, preferably running parallel to the guide tube 4, welded in between plates.

EXAMPLE

In a reactor as shown in FIG. 1 having a reaction volume of about 0.05 m$^3$ and provided with 36 parallel Field tubes which have a total cooling area of about 2.5 m$^3$ and into which a cooling water stream of about 1 m$^3$/h and having a temperature of about 35° C. is fed, 30.3 kg/h of propionaldehyde are introduced at 75° C. into a fast-flowing mixture consisting of about 84% of propionic acid, about 15% of propionaldehyde and not more than 1% of by-products, in particular organic acids and alcohols, by means of a metering pump. A pressure of 23 bar is set in the reactor by simultaneous introduction of 31 standard m$^3$/h. To maintain the loop flow, a volume of 2.5 m$^3$/h is circulated around the external product circuit. The pressure in the jet nozzle is about 3 bar above the reactor pressure and the specific power input is about 5 kW/m$^3$.

The reaction proceeds under virtually isothermal conditions, since the heat of reaction is removed where it arises. The maximum reaction temperature in the lower third of the reactor is 76° C.

A substream of 38.8 kg/h of the reaction mixture consisting of 84% of propionic acid, about 15% of propionaldehyde and less than 1% of by-products, in particular organic acids and alcohols, is taken off continuously. This corresponds to a space-time yield of 650 kg/m$^3$h. The unreacted propionaldehyde can be separated off by thermal means, in particular by distillation, or reacted further in a cascade of two reactors according to the present invention connected in series with additional use of a reaction tube. When using a cascade of two reactors according to the present invention, the total propionaldehyde conversion is 98.7% at a selectivity of about 96%.

We claim:

1. A reactor (1) of high cylindrical construction for continuously carrying out gas-liquid-solid reactions, provided with a downward-directed jet nozzle (2) via which the starting materials and the reaction mixture are fed in and which is located in the upper region of the reactor, and provided with an offtake (3), preferably in the lower region of the reactor, via which the reaction mixture is conveyed via an external circuit back to the jet nozzle (2) by means of a pump (P), where a guide tube (4) which extends essentially over the total length of the reactor (1) with the exception of the reactor ends and has a cross-sectional area in the range from one tenth to one half of the cross-sectional area of the reactor (1) is located concentrically in the reactor (1), and the jet nozzle (2) is located above the upper end of the guide tube (4), preferably at a distance of from one eighth of the guide tube diameter to one guide tube diameter, or projects into the guide tube (4) to a depth up to a plurality of guide tube diameters, and a heat exchanger provided with heat exchange tubes is integrated into the annular space, wherein the heat exchanger tubes run parallel to the guide tube (4).

2. A reactor (1) as claimed in claim 1, wherein the heat exchanger tubes of the heat exchanger are welded in between plates.

3. A reactor (1) as claimed in claim 1, wherein the jet nozzle (2) is configured as a single-fluid nozzle and, optionally, a facility for introducing one or more gaseous reactants, preferably one or more, in particular from one to three, annular pipes having a plurality of orifices, in particular in the lower region of the reactor or distributed over the height of the reactor, is (are) additionally provided in the annular space between guide tube (4) and interior wall of the reactor.

4. A reactor (1) as claimed in claim 1, wherein the jet nozzle (2) is configured as a three-fluid or two-fluid nozzle.

5. A reactor (1) as claimed in claim 1, which has an aspect ratio 1/d of from 3 to 10, preferably from 6 to 10.

6. A reactor (1) as claimed in claim 1, wherein the ratio of the diameters of guide tube (4) and reactor (1) is in the range from 0.25 to 0.5, particularly preferably in the range from 0.28 to 0.33.

7. A reactor (1) as claimed in claim 1, wherein an impingement plate (6) is located in the region of the reactor below the lower end of the guide tube (4), preferably at a distance of one guide tube diameter.

8. A continuous process for carrying out gas-liquid or gas-liquid-solid reactions in a reactor (1) as claimed in claim 1, wherein the major part of the reaction mixture, corresponding to from 2 to 30 times, preferably from 5 to 10 times, the volume flow of the reaction mixture pumped around the external circuit flows in an internal loop through the guide tube (4) from the top downward and through the annular space between guide tube (4) and interior wall of the reactor from the bottom upward.

9. A process as defined in claim 8, wherein the reaction is a strongly exothermic gas-liquid or gas-liquid-solid for hydrogenation, oxidation, ethoxylation, propoxylation, hydroformylation or aldol condensation reaction.

* * * * *